United States Patent
Maruyama et al.

(10) Patent No.: US 8,445,031 B2
(45) Date of Patent: May 21, 2013

(54) METHOD FOR PRODUCING PURIFIED TEA EXTRACT

(75) Inventors: Eizo Maruyama, Kamisu (JP); Hideaki Ueoka, Kamisu (JP); Keiji Shibata, Kamisu (JP)

(73) Assignee: Kao Corporation, Tokyo (JP)

(*) Notice: Subject to any disclaimer, the term of this patent is extended or adjusted under 35 U.S.C. 154(b) by 85 days.

(21) Appl. No.: 12/676,281

(22) PCT Filed: Sep. 4, 2008

(86) PCT No.: PCT/JP2008/002432
§ 371 (c)(1),
(2), (4) Date: Mar. 3, 2010

(87) PCT Pub. No.: WO2009/031306
PCT Pub. Date: Mar. 12, 2009

(65) Prior Publication Data
US 2010/0184167 A1 Jul. 22, 2010

(30) Foreign Application Priority Data
Sep. 5, 2007 (JP) ................................. 2007-230067

(51) Int. Cl.
*A61K 36/00* (2006.01)
*A61K 36/82* (2006.01)
*C12P 1/00* (2006.01)
*C12P 1/02* (2006.01)

(52) U.S. Cl.
USPC .............. 424/725; 424/729; 435/41; 435/171

(58) Field of Classification Search
None
See application file for complete search history.

(56) References Cited

U.S. PATENT DOCUMENTS

| | | | |
|---|---|---|---|
| 4,673,530 A | 6/1987 | Hara | |
| 2006/0057261 A1 | 3/2006 | Ogura et al. | |
| 2006/0263454 A1* | 11/2006 | Sugiyama et al. | 424/729 |
| 2007/0128327 A1 | 6/2007 | Takashima et al. | |
| 2007/0178175 A1 | 8/2007 | Matsubara et al. | |
| 2009/0041921 A1 | 2/2009 | Maruyama et al. | |

FOREIGN PATENT DOCUMENTS

| | | |
|---|---|---|
| CN | 1708238 | 12/2005 |
| JP | 59 219384 | 12/1984 |
| JP | 1 289447 | 11/1989 |
| JP | 3 133928 | 6/1991 |
| JP | 8 109178 | 4/1996 |
| JP | 2002 335911 | 11/2002 |
| JP | 2004 222719 | 8/2004 |
| JP | 2004 321105 | 11/2004 |
| JP | 2006 63004 | 3/2006 |
| JP | 2006 160656 | 6/2006 |
| JP | 2006 288383 | 10/2006 |
| JP | 2007 89561 | 4/2007 |
| JP | 2007 104967 | 4/2007 |
| JP | 2007104967 A * | 4/2007 |
| JP | 2007195458 A * | 8/2007 |
| JP | 2007195479 A * | 8/2007 |
| WO | 2005 053415 | 6/2005 |
| WO | 2005 077384 | 8/2005 |

OTHER PUBLICATIONS

Wang et al, Preparation of high purity epigallocatechin gallate by polyamide packed chromatographic column separation. Yingyong Huaxue (2007), 24(4), 443-447.*
Office Action issued Aug. 31, 2012, in Chinese Patent Application No. 200880105761.6 (with English-language Translation).
Office Action issued Sep. 18, 2012, in Japanese Patent Application No. 2009-531128 (with English-language Translation).
Qi Jinghua et al., "Study on Adsorption of Polyphenol and Haze Substances in Apple Juice by Active Carbon", Food and Fermentation Industry, May 30, 2003, vol. 29, No. 4, pp. 11-14, discussed in the English translation of the Chinese Office Action submitted herewith.
Office Action issued Jan. 31, 2013, in Chinese patent application No. 200880105761.6 (w/English translation).

* cited by examiner

*Primary Examiner* — Qiuwen Mi
(74) *Attorney, Agent, or Firm* — Oblon, Spivak, McClelland, Maier & Neustadt, L.L.P.

(57) ABSTRACT

A purified tea extract is improved in taste by reducing a percentage of gallates in the non-polymer catechins. A process according to the present invention for the production of a purified tea extract includes subjecting a tea extract to a hydrolysis treatment, causing the tea extract to adsorb on the activated carbon, and then bringing a basic aqueous solution or an aqueous solution of an organic solvent into contact with the activated carbon to elute the non-polymer catechins.

14 Claims, No Drawings

METHOD FOR PRODUCING PURIFIED TEA EXTRACT

FIELD OF THE INVENTION

The present invention relates to a process for producing a purified tea extract with a reduced percentage of gallate forms in non-polymer catechins.

BACKGROUND OF THE INVENTION

Catechin is reported to possess an α-amylase-activity-inhibiting effect as one of its physiological properties (see Patent Document 1). In order for such a physiological effect to materialize, a large amount of catechin needs to be ingested more conveniently, so there has been a strong demand for a method by which a high concentration of the catechin can be added to a beverage.

Employed as one of such methods is to add the catechin in a dissolved form to a beverage by making use of a tea extract such as a concentrate of green tea extract (Patent Document 2). However, depending on the kind of the beverage to which the catechin is to be added in the high concentration by this method, for example, when catechin is added to a black tea extract solution or a carbonated beverage, the residual bitterness and astringency intrinsic to the caffeine and the green tea are known to considerably impair the commercial value of the beverage.

It has been known for years that an application of tannase treatment to an extract solution of fermented tea such as black tea, can inhibit a suspension, in other words, the formation of tea cream when cooled at low temperatures. According to a method that subjects the green tea extract solution to tannase treatment as disclosed in Patent Document 3, it is possible to reduce the percentage of gallate forms, which are a cause of bitterness, in the non-polymer catechins. Further, as methods for removing impurities such as caffeine from tea extracts, adsorption methods (Patent Documents 4-6), an extraction method (Patent Document 7) and the like are known.

Patent Document 1: JP-A-03-133928
Patent Document 2: JP-A-59-219384
Patent Document 3: JP-A-2004-321105
Patent Document 4: JP-A-2004-222719
Patent Document 5: JP-A-08-109178
Patent Document 6: JP-A-2002-335911
Patent Document 7: JP-A-01-289447

SUMMARY OF THE INVENTION

The present invention provides a process for producing a purified tea extract, including hydrolyzing a tea extract, causing the tea extract to adsorb on activated carbon, and then bringing a basic aqueous solution or an aqueous solution of an organic solvent into contact with the activated carbon to elute non-polymer catechins.

DETAILED DESCRIPTION OF THE INVENTION

As described above, the treatment of a tea extract with tannase can reduce gallate forms, which become a cause of bitterness, in non-polymer catechins. However, new problems such as sourness and harshness have arisen. It has come to the knowledge of the present inventors that these new problems are caused by the conversion of the tea extract into a mixture of non-polymer catechins and gallic acid by the tannase treatment.

The present invention is to provide a process for the production of a purified tea extract, which is high in the recovery rate of non-polymer catechins and is reduced in the percentage of gallate forms in the non-polymer catechins and also in caffeine and gallic acid.

The present inventors conducted research as to the purification treatment of non-polymer catechins in a tea extract. As a result, it has been found that a tea extract, which is reduced in the percentage of gallate forms in non-polymer catechins, is also reduced in the content of the caffeine and also the byproduced gallic acid, and is hence improved in taste, can be obtained by conducting a first step that subjects the starting tea extract to the hydrolysis treatment to degrade the gallate forms in the non-polymer catechins into free non-polymer catechins and gallic acid to reduce the percentage of gal late forms in the non-polymer catechins, and also, and a second step that after the hydrolysis treatment, passes the tea extract through the activated carbon to allow the non-polymer catechins to adsorb once them on the activated carbon and then elutes the adsorbed non-polymer catechins with a basic aqueous solution or an aqueous solution of an organic solvent.

According to the present invention, the percentage of gallate forms in non-polymer catechins is reduced, and moreover, the content of caffeine and the amount of gallic acid byproduced upon hydrolysis treatment are significantly reduced, as compared to those before treatment. Therefore, a purified tea extract with an improved taste can be obtained.

The term "non-polymer catechins" as used herein is a generic term, which collectively encompasses non-epicatechins such as catechin, gallocatechins, catechingallates and gallocatechingallates, and epicatechins such as epicatechins, epigallocatechins, epicatechingallates and epigallocatechingallates.

The term "gallate forms in non-polymer catechins" as used herein is a generic term, which collectively embraces catechingallates, gallocatechingallates, epicatechingallates, epigallocatechingallates and the like.

As tea extracts usable in the present invention, extract solutions obtained from tea leaves such as green tea, black tea and oolong tea can be mentioned. Mixtures of caffeine-containing extracts derived from other caffeine-containing plants such as, coffees with tea extract solutions are also usable. Usable tea leaves, more specifically, include tea leaves prepared from tea leaves of the Genus *Camellia*, for example, *C. sinensis*, *C. assamica* and the Yabukita variety, or their hybrids. Such prepared tea leaves include green teas such as sencha (middle-grade green tea), bancha (coarse green tea), gyokuro (shaded green tea), tencha (powdered tea) and kamairicha (roasted tea). It is also possible to use tea leaves subjected to treatment in contact with carbon dioxide in its supercritical state. As a tea extract for use in the present invention, a green tea extract is preferred from the standpoint of the content of non-polymer catechins.

The extraction from tea leaves is by stirring extraction while using water, a water-soluble organic solvent or a mixture thereof as an extraction solvent. Upon extraction, organic acid salts or an organic acid such as sodium ascorbate, can be added beforehand to the water, the water-soluble organic solvent or the mixture thereof. It is also possible to make combined use of a boiling deaeration or an extraction method which is conducted while bubbling an inert gas such as nitrogen gas to eliminate dissolved oxygen, that is, under the so-called non-oxidizing atmosphere. The extract solution obtained as described above can be used in the present invention as it is or after it is dried or concentrated. Exemplary forms of the tea extract include liquid, slurry, semi-solid and solid forms.

Instead of employing, as a tea extract for use in the present invention, an extract solution obtained from tea leaves, it is also possible to employ a concentrate of tea extract in a form dissolved in water or an organic solvent or diluted with water or an organic solvent. It is also possible to employ an extract solution from tea leaves and the concentrate of tea extract in combination.

The term "a concentrate of tea extract" as used herein means a concentrate of an extract obtained from tea leaves with hot water or a water-soluble organic solvent, and means, for example, those prepared by the processes disclosed in JP-A-59-219384, JP-A-04-020589, JP-A-05-260907, JP-A-05-306279 and the like. As a specific green tea extract, it is possible to use, as a solid green tea extract, a commercially-available crude catechin preparation such as "POLYPHE-NON" (product of Tokyo Food Techno Co., Ltd.), "TEAFU-RAN" (product of ITO EN, LTD.) or "SUNPHENON" (product of Taiyo Kagaku Co., Ltd.).

In the present invention, the tea extract is first subjected to hydrolysis treatment. By the hydrolysis treatment, the percentage of gallate forms in the non-polymer catechins is reduced. The reduction in the percentage of gallate forms in the non-polymer catechins by the hydrolysis may be preferably 5 wt % or more, more preferably 7 wt % or more, far more preferably 10 wt % or more, as compared to the percentage of gallate forms before hydrolysis, from the standpoint of taste improvements. As the manner of hydrolysis, the hydrolysis treatment can be conducted by a treatment with enzymes, an acid treatment, an alkali treatment, or the like. The enzymes may preferably be an enzyme, a fungus, a culture or the like having a tannase activity. The acid may preferably be hydrochloric acid, sulfuric acid, phosphoric acid or the like, and the alkali may preferably be caustic soda or the like. Among these, the hydrolysis with enzymes or the like is preferred from the standpoint of reaction control. The term "having tannase activity" as used herein means to have activities capable of degrading tannin, and any desired enzymes, fungi or cultures can be used as long as they have such activities.

More specifically, among products commercially available as enzymes having tannase activity, "PECTINASE PL AMANO" (product of Amano Enzyme Inc.), "HEMISEL-LULASE AMANO 90" (product of Amano Enzyme Inc.), "TANNASE KTFH" (product of Kikkoman Corporation), and the like can be used. Of these, tannase is preferred. As such tannase, tannase obtainable by culturing, for example, a tannase-producing fungus of the *Aspergillus, Penicillium* or *Rhizopus* genus can be mentioned. More preferred is tannase available from *Aspergillus oryzae*.

The term "fungus having tannase activity" means the fungus that can produce an enzyme having tannase activity, and can include koji fungi or the like. For example, those of the *Aspergillus, Penicillium* or like genus can be mentioned, with *Aspergillus oryzae* being preferred.

The term "a culture having tannase activity" means a culture obtainable by cultivating a tannase-producing fungus of the *Aspergillus, Penicillium* or *Rhizopus* genus. As such a culture, a culture obtainable by conducting cultivation while using tannic acid as a sole carbon source can be mentioned preferably. The culture is usable no matter whether it is a purified product or an unpurified product.

From the standpoints of suppressions of flavor and taste deteriorations and productivity, it is preferred to complete the hydrolysis in a time as short as possible. For this purpose, the use of an enzyme or culture is preferred.

The enzyme or culture, which has tannase activity and is to be used in the present invention, may preferably have an enzyme activity of from 500 to 100,000 U/g. An enzyme activity lower than 500 U/g requires a great deal of enzyme in order to complete the treatment in an industrially-limited time, while an enzyme activity higher than 100,000 U/g leads to an excessively high enzyme reaction rate and hence, is difficult to control the reaction system. It is to be noted that "1 Unit" indicates an amount of enzyme that hydrolyses 1 micromole of ester bonds, which are contained in tannic acid, in water of 30° C.

The concentration of non-polymer catechins upon conducting treatment with an enzyme or culture having tannase activity may be preferably from 0.1 to 22 wt %, more preferably from 0.1 to 15 wt %, far more preferably from 0.5 to 10 wt %, still far more preferably from 0.5 to 3 wt %. A concentration lower than 0.1 wt % leads to a reduction in the amount of the tea extract adsorb on the activated carbon after its hydrolysis, while a concentration higher than 22 wt % requires a long time for the hydrolysis treatment. Concentrations outside the above range are, therefore, not preferred from the standpoints of productivity and the taste of the tea extract.

In order to obtain such a percentage of gallate forms in the non-polymer catechins as being capable of realizing an improvement in taste, it is preferred to add the enzyme or culture such that it falls within a range of from 0.01 to 10 wt % based on the non-polymer catechins in the tea extract. In order to complete the above-described hydrolysis treatment, including the step of inactivating the enzyme, in an industrially-optimal enzyme reaction time, the concentration of the enzyme or culture may be preferably from 0.01 to 7 wt %, more preferably from 0.03 to 5 wt %.

The enzyme or culture having tannase activity may be added preferably at from 1 to 300 Units/g-non-polymer catechins, more preferably at from 3 to 200 Units/g-non-polymer catechins, still more preferably at from 5 to 150 Units/g-non-polymer catechins, all, based on the non-polymer catechins in the green tea extract.

The temperature of the treatment with the enzyme or culture may be preferably from 0 to 70° C. in which optimal enzyme activity is available, with from 0 to 60° C. being more preferred and from 5 to 50° C. being still more preferred.

For the termination of the hydrolysis reaction conducted with the enzyme or culture, it is necessary to inactivate the enzyme. This enzyme inactivation can be achieved by heating. The enzyme inactivation temperature may be from 70 to 100° C.

As an inactivation method of the enzyme, it is possible to terminate the enzyme reaction by conducting heating batch-wise or in such a continuous manner as in a plate-type heat exchanger. Further, the tea extract can be clarified by an operation such as centrifugation subsequent to the completion of the inactivation of the tannase.

When a koji fungus is used as the fungus, for example, hydrolysis treatment is conducted by placing the koji fungus in a tea extract containing non-polymer catechins at a concentration of preferably from 0.1 to 22 wt %, more preferably from 0.1 to 15 wt %, still more preferably from 0.5 to 15 wt %. The koji fungus may be added generally in a range of from 0.5 wt % to 10 wt %, preferably in a range of from 1.0 wt % to 5 wt %, both, based on the non-polymer catechins in the tea extract, depending on the kind or the like of the koji fungus. As temperature conditions, from 45 to 70° C. is preferred, with from 50 to 60° C. being more preferred. The fermentation time may be generally from 12 hours to 20 days, preferably from 1 day to 10 days. The inactivation of the enzyme activity of the koji fungus is effected likewise as done at the time of the termination of the hydrolysis reaction conducted with the enzyme or culture.

After the hydrolysis, the tea extract is then allowed to adsorb on the activated carbon. After the adsorption and before the basic aqueous solution or the aqueous solution of the organic solvent is brought into contact, the activated carbon may preferably be washed to remove gallic acid and impurities which are contained in the activated carbon. The basic aqueous solution or the aqueous solution of the organic solvent is then brought into contact to elute non-polymer catechins. By the treatment with the activated carbon, caffeine and gallic acid can be reduced. In the present invention, it is unnecessary to intervene absorption/desorption treatment with another adsorbent, for example, a synthetic adsorbent between the hydrolysis step and the activated carbon treatment step.

On the activated carbon to be used, no particular limitation is imposed insofar as it is generally used on an industrial scale. Usable examples include commercially-available products such as "ZN-50", "Y-10S", "GS-1", "GS-B" (product of Ajinomoto Fine-Techno Co., Ltd.); "KURARAY COAL GLC", "KURARAY COAL PK-D", "KURARAY COAL PW-D", "KURARAY COAL GW", "KURARAY COAL GA", "KURARAY COAL GA-D", "KURARAY COAL RP-15" (products of Kuraray Chemical Co., Ltd.); "SHIRASAGI AW50", "SHIRASAGI A", "SHIRASAGI P", "SHIRASAGI KL", "SHIRASAGI M", "SHIRASAGI C", "CARBORAFIN", "WH2C" (Japan Envirochemicals, Ltd.); "GM130A", "CW130A", "CW130AR", "CW350AR", "GL130A", "SG", "SGA", "SGP" (products of Futamura Chemical Co., Ltd.); "YASHIKORU", "MAS BRAND", "BAIHO BRAND", "BAIHO F BRAND" (product of Taihei Chemical Industrial Co., Ltd.); and "CPG", "CAL", "S80A" (products of Calgon Mitsubishi Chemical Corporation).

From the standpoint of achieving efficient adsorption of non-polymer catechins, the activated carbon to be described hereinafter is preferred. The average pore size may be preferably from 0.5 to 10 nm (nanometers), more preferably from 1.0 to 9.0 nm (nanometers), still more preferably from 2.0 to 8.0 nm (nanometers). The pore volume may be preferably from 0.01 to 2.5 mL/g, more preferably from 0.1 to 2.0 mL/g, still more preferably from 0.5 to 1.7 mL/g. The specific surface area may be in a range of preferably from 800 to 2,000 $m^2/g$, more preferably from 900 to 1,600 $m^2/g$, still more preferably from 1,000 to 1,500 $m^2/g$. It is to be noted that these physical values are values based on the nitrogen adsorption method.

As a method for allowing the tea extract to adsorb on the activated carbon after the hydrolysis treatment, it is possible to adopt a batch method that adds the activated carbon to the tea extract after the hydrolysis treatment, stirs the mixture for adsorption, and recovers the activated carbon by a filter operation; or a column method that continuously conducts adsorption treatment by using a column packed with the activated carbon. From the standpoint of productivity, however, the continuous treatment method by using the column is preferred.

As a method for allowing the tea extract to adsorb on the activated carbon after the hydrolysis treatment, it is preferred to pass the tea extract through a column packed with the activated carbon. As conditions for passing the tea extract through the column packed with the activated carbon, it is preferred to pass the tea extract at a flow rate of SV (space velocity)=0.5 to 10 $[h^{-1}]$ and at a flow ratio of from 0.5 to 20 [v/v] to the activated carbon. A flow rate higher than 10 $[h^{-1}]$ or a flow ratio greater than 20 [v/v] may lead to insufficient or unstable adsorption of the non-polymer catechins.

When washing the activated carbon after the tea extract is allowed to adsorb on the activated carbon subsequent to its hydrolysis treatment, an aqueous solution to be used for the washing may preferably have a pH of 7 or lower (25° C.; this will apply equally hereinafter) from the standpoint of the recovery rate of catechins, and a mixed system with a water-soluble organic solvent may also be used. As the water-soluble organic solvent, acetone, methanol, ethanol or the like can be mentioned, with ethanol being preferred from the viewpoint of use in foods. The concentration of the contained organic solvent may be preferably from 0 to 5 wt %, more preferably from 0 to 2 wt %, still more preferably from 0 to 1 wt % from the standpoint of the recovery rate of the non-polymer catechins.

It is preferred to remove gallic acid and impurities, which have adhered on the activated carbon, at a flow rate of SV (space velocity)=0.5 to 10 $[h^{-1}]$ and at a flow ratio of from 1 to 15 [v/v] to the activated carbon. From the standpoints of removal of gallic acid and impurities and the recovery rate of the non-polymer catechins, it is more preferred to conduct the washing at a flow rate of SV=0.5 to 5 $[h^{-1}]$ and at a flow ratio of from 1 to 7 [v/v].

As the basic aqueous solution for use in the elution of the non-polymer catechins, an alkaline aqueous solution of an alkali metal salt or alkaline earth metal salt is preferred, with a sodium-containing alkaline aqueous solution, for example, an aqueous solution of sodium hydroxide, an aqueous solution of sodium carbonate or the like being usable more preferably. The pH of the alkaline aqueous solution may preferably be in a range of from 7 to 14, and from the standpoint of the recovery rate of non-polymer catechins, from 9 to 13.8 may be preferred, with from 10 to 13.5 being more preferred. As a sodium-containing aqueous solution of pH 7 to 14, a 4 wt % or lower aqueous solution of sodium hydroxide, a 1 N aqueous solution of sodium carbonate or the like can be mentioned. In the basic aqueous solution, a water-soluble organic solvent may be contained. From the standpoint of separability between caffeine and non-polymer catechins, the concentration of the organic solvent may be in a range of preferably from 0 to 90 wt %, more preferably from 0 to 50 wt %, still more preferably from 0 to 20 wt %.

As conditions for passing the basic aqueous solution through the column, it is preferred to elute the non-polymer catechins at a flow rate of SV (space velocity)=2 to 10 $[h^{-1}]$ and at a flow ratio from 1 to 30 [v/v] to the activated carbon. From the standpoints of productivity and the recovery rate of non-polymer catechins, it is more preferred to conduct the elution at a flow rate of SV=3 to 7 $[h^{-1}]$ and at a flow ratio of from 3 to 15 [v/v].

The activated carbon used in the present invention can be reused by employing a predetermined method after the purification treatment. Specifically, it is possible to mention a method that passes an organic solvent such as ethanol through to desorb insolubles such as caffeine adsorbed on the activated carbon or that passes a high-concentration aqueous solution of an alkali such as sodium hydroxide through to conduct washing such that water-soluble components remaining on the activated carbon are all desorbed. Additionally, washing with steam may be combined further.

In the elution step, two or more basic aqueous solutions different in pH from each other can be used as the basic aqueous solutions for use in the elution, and in the ascending order of pH, these basic aqueous solutions can be brought into contact with the activated carbon. In each pH range, different non-polymer catechins and other components can be desorbed.

The eluate of non-polymer catechins is basic because they were eluted with the basic aqueous solution. From the viewpoint of the stability of non-polymer catechins, the pH of the eluate may be adjusted preferably to 7 or lower. Specifically, it is possible to use the neutralization with an acid, the removal of alkali metal ions by electrodialysis, or the removal of alkali metal ions with an ion exchange resin. From the simplicity of the process, it is preferred to adjust the pH with the ion exchange resin. As the ion exchange resin, the use of an $H^+$ cation-exchange resin is preferred. As the cation exchange resin, it is possible to use specifically "AMBERLITE 200CT, IR120B, IR124 or IR118", "DIAION SK1B, SK1BH, SK102, PK208 or PK212", or the like.

A description will next be made about the elution of non-polymer catechins with an aqueous solution of an organic solvent.

As the aqueous solution of the organic solvent for use in the elution of non-polymer catechins, an aqueous solution of acetone, methanol, ethanol or the like can be mentioned. Of these, ethanol is preferred from the viewpoint of use in foods. The concentration of the organic solvent contained may be preferably from 5 to 90 wt %, more preferably from 8 to 70 wt %, far more preferably from 10 to 50 wt % from the standpoint of separability from caffeine and color components.

It is preferred to elute the non-polymer catechins at a flow rate of SV (space velocity)=0.1 to 10 $[h^{-1}]$ and at a flow ratio of from 1 to 15 [v/v] to the activated carbon. From the standpoints of separability from caffeine and color components and the recovery rate of non-polymer catechins, it is more preferred to conduct the elution at a flow rate of SV=0.5 to 5 $[h^{-1}]$ and at a flow ratio of from 2 to 10 [v/v].

The eluate of non-polymer catechins may be subjected to subsequent steps after concentrating it as needed.

When the resultant eluate of non-polymer catechins is suspended, clarification is preferred. As a specific operation for the clarification, it can be mentioned to separate the solid portion and the water-soluble portion from each other by filtration and/or centrifugation.

The purified tea extract obtained by the present invention contains non-polymer catechins at from 25 to 95 wt %, preferably at from 40 to 95 wt %, more preferably at from 50 to 90 wt %, still more preferably at from 55 to 80 wt % in its solid content.

From the standpoint of a reduction of bitterness in non-polymer catechins, the percentage of gallate forms, which consist of catechingallates, epicatechingallates, gallocatechingallates and epigallocatechingallates, in the whole non-polymer catechins in the purified tea extract obtained by the present invention may be preferably from 0 to 70 wt %, more preferably from 0 to 50 wt %, far more preferably from 0 to 40 wt %.

From the standpoint of improving the taste, the concentration of caffeine in the purified tea extract obtained in the present invention may be, based on non-polymer catechins, at a caffeine/non-polymer catechins (weight ratio)=preferably 0 to 0.14, more preferably 0 to 0.1, far more preferably from 0 to 0.05, still far more preferably 0 to 0.035.

From the standpoint of tastes such as bitterness and sourness, the concentration of gallic acid in the purified tea extract obtained in the present invention may be, based on non-polymer catechins, at a gallic acid/non-polymer catechins (weight ratio)=preferably 0 to 0.1, more preferably 0 to 0.08, far more preferably from 0 to 0.06.

Preferred, as the purified tea extract obtainable by the present invention, from the standpoint of improving the taste, is such a purified tea extract that non-polymer catechins in the solid content account for from 25 to 95 wt %, the percentage of gallate forms in the non-polymer catechins is from 0 to 70 wt %, preferably from 0 to 50 wt %, the gallic acid/non-polymer catechins (weight ratio) is from 0 to 0.1, and the caffeine/non-polymer catechins (weight ratio) is from 0 to 0.14.

For providing a beverage with improved color-tone stability, the eluate of non-polymer catechins may preferably be decolorized. As a specific decolorization operation, it is possible to mention a method that conducts decolorization by performing membrane separation or by dispersing or dissolving a tea extract in an aqueous solution of an organic solvent and bringing the dispersion or solution into contact with activated clay and/or acid clay.

The purified tea extract obtained by the present invention can be used as it is. The solvent may be removed by a method such as reduced-pressure concentration or thin-film concentration. When the powder is desired as the product form of the tea extract, the tea extract can be formed into the powder by a method such as spray drying or freeze drying.

The purified tea extract obtained by the present invention can be added to a packaged beverage. As a usable package, a package of a conventional form, such as a molded package made of polyethylene terephthalate as a principal component (a so-called PET bottle), a metal can, a paper package combined with metal foils or plastic films, a bottle, can be mentioned. The term "packaged beverage" as used herein means one that can be taken without dilution.

The above-described packaged beverage can be produced, for example, by filling the beverage in a package such as a metal can and, when heat sterilization is feasible, conducting heat sterilization in the Food Sanitation Act. For those which cannot be subjected to the retort sterilization like PET bottles or paper packages, a process is adopted such that the beverage is sterilized beforehand at a high temperature for a short time under similar sterilization conditions as those described above, for example, by a plate-type heat exchanger or the like, is cooled to a particular temperature, and is then filled in the package. Under aseptic conditions, additional components may be added to and filled in the beverage-filled package.

EXAMPLES (Measurement Methods of Catechins, Caffeine and Gallic Acid)

A high-performance liquid chromatograph (model: "SCL-10AVP") manufactured by Shimadzu Corporation was used. The chromatograph was fitted with a liquid chromatograph column packed with octadecyl group-introduced silica gel, "L-Column, TM ODS" (4.6 mm in diameter×250 mm; product of Chemicals Evaluation and Research Institute, Japan). A sample solution was filtered through a filter (0.45 μm), and then subjected to chromatography at a column temperature of 35° C. by the gradient elution method. As a standard product of the catechins, the product of Mitsui Norin Co., Ltd. was used, and quantification was performed by a calibration line method. A mobile phase, Solution A, was a solution containing acetic acid at 0.1 mol/L in distilled water, while another mobile phase, Solution B, was a solution containing acetic acid at 0.1 mol/L in acetonitrile. The measurement was conducted under the conditions of 20 μL sample injection volume and 280 nm UV detector wavelength.

(Assessment of Flavor and Taste after Sterilization)

The tea extract obtained in each Examples was diluted with deionized water such that the content of non-polymer catechins was lowered to 0.175% [w/v]. An aliquot (40 mL) of the diluted tea extract was placed in a 50-mL pressure-resistant glass vessel. 0.1 wt % of sodium ascorbate was added thereto. The solution was adjusted to pH 6.4 with a 5% aqueous solution of sodium bicarbonate, purged with nitrogen, and then subjected to thermal sterilization at 121° C. for 10 minutes in an autoclave. Subsequently, it was determined by a panel of 5 trained assessors as to whether or not bitterness, sourness or coarseness derived from green tea was felt.

(Assessment of Bitterness by the Quinine Sulfate Method (the Equivalent Concentration Test Method))

Quinine sulfate dihydrate was adjusted to concentrations corresponding to the bitterness intensities shown in Table 1. After each assessment sample was tasted, a determination was made concerning which sample of the standard bitterness solutions corresponds to the intensity of bitterness of the assessed sample. The intensity of bitterness was confirmed by the panel of five trained assessors.

(References: Newly-edited "Organoleptic Test Handbook" in Japanese, PP 448-449, Organoleptic Test Committee, Union of Japanese Scientists and Engineers; Perception & Psychophysics, 5, pp. 347-351, 1696).

TABLE 1

Concentrations of Standard Bitterness Solutions

| Bitterness intensity | Quinine sulfate dihydrate (g/100 mL, ap.) |
|---|---|
| 1 | 0.00023 |
| 2 | 0.00050 |
| 3 | 0.00094 |
| 4 | 0.00157 |
| 5 | 0.00241 |
| 6 | 0.00388 |
| 7 | 0.00608 |
| 8 | 0.00985 |
| 9 | 0.01572 |
| 10 | 0.02568 |

(Measurement of Color Tone)

Using a HITACHI spectrophotometer (Model: U-2001), the sample was diluted with deionized water in a glass cell to provide an aqueous solution in which the concentration of non-polymer catechins was 175 mg/100 mL, and was then measured. The measurement wavelength of the spectrophotometer at the time of the analysis was set at 450 nm.

Example 1

Hot water of 88° C. (45 kg) was added to the green tea leaves (produce of Kenya, large leaf variety; 3 kg). After batchwise extraction for 60 minutes under stirring, coarse filtration was conducted through a 100-mesh screen. To remove fine powder from the extract solution, a centrifugal separation operation was then performed to obtain a "green tea extract solution 1" (37.2 kg, pH 5.4) (the concentration of non-polymer catechins in the green tea extract solution=0.89 wt %, the percentage of gallate forms in the non-polymer catechins=52.3 wt %, the content of caffeine: 0.17 wt %).

The green tea extract solution was held at a temperature of 15° C., and tannase ("TANNASE KTFH", product of Kikkoman Corporation; 500 U/g) was then added to the green tea extract solution to give a concentration of 430 ppm. The solution was held for 55 minutes. When the percentage of gallate forms had dropped to 32 wt %, the solution was heated to 90° C., at which the solution was held for 2 minutes to inactivate the enzyme so that the reaction was terminated (pH 5.2). Under the conditions of 70° C. and 6.7 kPa, concentration processing was performed to a Brix concentration of 20% by reduced-pressure concentration. Further, the concentrate was spray-dried to obtain a powdery "tannase-treated green tea extract 1" (0.9 kg). The resulting green tea extract had the following data—the content of non-polymer catechins: 29.0 wt %, the percentage of gallate forms in the non-polymer catechins: 31.7 wt %, the content of caffeine: 5.86 wt %, and the content of gallic acid: 3.09 wt %.

The "tannase-treated green tea extract 1" (10 g) was dissolved under stirring at 25° C. for 30 minutes in deionized water (300 g) (tannase-treated solution (1)). The resulting tannase-treated solution had the following data—the content of non-polymer catechins: 0.94 wt %, the percentage of gallate forms in the non-polymer catechins: 31.7 wt %, the content of caffeine: 0.19 wt %, and the content of gallic acid: 0.1 wt %.

Activated carbon, "TAIKO SGP" (product of Futamura Chemical Co., Ltd.; 40 mL) was packed in a stainless steel column 1 (22 mm inner diameter×105 mm height, volume: 40 mL). An ion-exchange resin "SK1BH" (product of Mitsubishi Chemical Corporation; 16 mL) was packed in a stainless steel column 2 (22 mm inner diameter×42 mm height, volume: 16 mL). The tannase-treated solution (1) (200 g, 5 times volume relative to the activated carbon) was passed at SV=2 ($h^{-1}$) through the column 1, and the outflow was discarded. The column 1 was then washed at SV=2 ($h^{-1}$) with water (80 mL, 2 times volume relative to the activated carbon). After washing it with water, a 0.1 wt % aqueous solution of sodium hydroxide (pH 12.5; 600 mL, 15 times volume relative to the activated carbon) was passed at SV=5 ($h^{-1}$) to obtain an eluate. The eluate was continuously passed through the stainless steel column 2 to effect deionization, so that a purified tea extract (591 g; pH 3.1) was obtained. Non-polymer catechins were contained at 0.24 wt % in the purified tea extract, the recovery rate of non-polymer catechins from the tannase-treated solution (1) was 77%, and the percentage of gallate forms in the non-polymer catechins was 32 wt %. Further, the content of caffeine was 0 wt %, and the content of gallic acid was 0.01 wt %. Non-polymer catechins in the solid content of the purified tea extract amounted to 58 wt %.

Example 2

The "tannase-treated green tea extract 1" (30 g) obtained in Example 1 was dissolved under stirring at 25° C. for 30 minutes in deionized water (900 g) (tannase-treated solution (2)). The resulting tannase-treated solution had the following data—the content of non-polymer catechins: 0.94 wt %, the percentage of gallate forms in the non-polymer catechins: 30.6 wt %, the content of caffeine: 0.19 wt %, and the content of gallic acid: 0.11 wt %.

Activated carbon, "KURARAY COAL GLC" (product of Kuraray Chemical K.K.; 125 mL) was packed in a stainless steel column 3 (35 mm inner diameter×130 mm height, volume: 125 mL). Anion-exchange resin "SK1BH" (product of Mitsubishi Chemical Corporation; 50 mL) was packed in a stainless steel column 4 (22 mm inner diameter×132 mm height, volume: 50 mL). The tannase-treated solution (2) (750 g, 6 times volume relative to the activated carbon) was passed at SV=2 ($h^{-1}$) through the column 3, and the outflow was discarded. The column 3 was then washed at SV=2 ($h^{-1}$) with water (625 mL, 5 times volume relative to the activated carbon). After washing it with water, a 0.1 wt % aqueous solution of sodium hydroxide (pH 12.5; 900 mL, 7.2 times volume relative to the activated carbon) was passed at SV=5 (h$^{-1}$) to obtain an eluate. The eluate was continuously passed through the stainless steel column 4 to effect deionization, so that a purified tea extract (897 g; pH 2.8) was obtained. Non-polymer catechins were contained at 0.57 wt % in the purified tea extract, the recovery rate of non-polymer catechins from the tannase-treated solution (2) was 72%, and the percentage of gallate forms in the non-polymer catechins was 30.4 wt %. Further, the content of caffeine was 0 wt %, and the content of gallic acid was 0.02 wt %. Non-polymer catechins in the solid content of the purified tea extract amounted to 56 wt %.

Comparative Example 1

Hot water of 90° C. (27 kg) was added to the green tea leaves (Yunnan Province, China; large leaf variety; 1.8 kg). After batchwise extraction for 30 minutes under stirring, coarse filtration was conducted through a 100-mesh screen. Subsequent to a centrifugal separation operation, filtration was conducted through No. 2 filter paper to obtain a "green tea extract solution 2" (20.4 kg, pH 5.3) (the concentration of non-polymer catechins in the green tea extract solution=0.96 wt %, the percentage of gallate forms in the non-polymer catechins=69.5 wt %, caffeine=0.24 wt %, gallic acid=0.01 wt %).

The green tea extract solution was set to a temperature of 25° C., and tannase ("TANNASE KTFH", product of Kikkoman Corporation; 500 U/g) was then added to the green tea extract solution to give a concentration of 300 ppm. The solution was held for 85 minutes. When the percentage of gallate forms had dropped to 52.4 wt %, the solution was heated to 90° C., at which the solution was held for 2 minutes to inactivate the enzyme so that the reaction was terminated (pH 4.8). The resulting tannase-treated solution had the following data—the content of non-polymer catechins: 0.89 wt %, the percentage of gallate forms in the non-polymer catechins: 52.4 wt %, the content of caffeine: 0.20 wt %, and the content of gallic acid: 0.10 wt %. Non-polymer catechins in the solid content of the tannase-treated solution amounted to 32.3 wt %.

Comparative Example 2

By a similar procedure as in Example 1, a "green tea extract solution 3" was obtained (the concentration of non-polymer catechins in the green tea extract solution=0.92 wt %, the percentage of gallate forms in the non-polymer catechins=51.1 wt %, caffeine=0.17 wt %).

Activated carbon, "KURARAY COAL GLC" (product of Kuraray Chemical K.K.; 32 mL) was packed in a resinous column (25 mm inner diameter×70 mm height, volume: 32 mL). An ion-exchange resin "SK1BH" (product of Mitsubishi Chemical Corporation; 16 mL) was packed in a stainless steel column 5 (22 mm inner diameter×45 mm height, volume: 17 mL). The "green tea extract solution 3" (192 g, 6 times volume relative to the activated carbon) was passed at SV=2 (h$^{-1}$) through the resinous column, and the outflow was discarded. A 1 wt % aqueous solution of sodium hydroxide (pH 14; 224 mL, 7 times volume relative to the activated carbon) was then passed at SV=5 (h$^{-1}$) through the column to obtain an eluate. The eluate was continuously passed through the stainless steel column 5 to effect deionization, so that a purified tea extract (232 g; pH 2.0) was obtained. Non-polymer catechins were contained at 0.49 wt % in the purified tea extract, the recovery rate of non-polymer catechins from the "green tea extract solution 3" was 65%, and the percentage of gallate forms in the non-polymer catechins was 48.6 wt %. Further, the content of caffeine was 0 wt %, and the content of gallic acid was 0.016 wt %. Non-polymer catechins in the solid content of the tea extract amounted to 56 wt %.

Comparative Example 3

The "green tea extract solution 1" obtained in Example 1 was held at a temperature of 15° C., and tannase ("TANNASE KTFH", product of Kikkoman Corporation; 500 U/g) was added to the green tea extract solution to give a concentration of 430 ppm. The solution was held for 55 minutes. When the percentage of gallate forms had dropped to 30.5 wt %, the solution was heated to 90° C., at which the solution was held for 2 minutes to inactivate the enzyme so that the reaction was terminated (pH 5.1).

Concentration processing was then performed under conditions of 70° C. and 6.7 kPa to a Brix concentration of 20% by reduced-pressure concentration. Further, the concentrate was spray-dried to obtain a powdery "tannase-treated green tea extract 2" (0.91 kg). The resulting green tea extract had the following data—the content of non-polymer catechins: 27.8 wt %, the percentage of gallate forms in non-polymer catechins: 30.3 wt %, the content of caffeine: 6.74 wt %, and the content of gallic acid: 3.58 wt %.

The "tannase-treated green tea extract 2" (285 g) was dissolved under stirring at 25° C. for 30 minutes in deionized water (8,550 g) (tannase-treated solution (3)). The resulting tannase-treated solution had the following data—the content of non-polymer catechins: 0.90 wt %, the percentage of gallate forms in non-polymer catechins: 30.3 wt %, the content of caffeine: 0.21 wt %, and the content of gallic acid: 0.11 wt %.

A synthetic adsorbent "SP-70" (product of Mitsubishi Chemical Corporation; 2,048 mL) was packed in a stainless steel column 6 (110 mm inner diameter×230 mm height, volume: 2, 185 mL). The tannase-treated solution (3) (8,191 g, 4 times volume relative to the synthetic adsorbent) was passed at SV=1 (h$^{-1}$) through the column 6, and the outflow was discarded. The column 6 was then washed at SV=2 (h$^{-1}$) with water (2,048 mL, same volume relative to the synthetic adsorbent). After washing it with water, a 20 wt % aqueous solution of ethanol (12,287 mL, 6 times volume relative to the synthetic adsorbent) was passed at SV=2 (h$^{-1}$) through the column to obtain a purified tea extract (12,090 g, pH 2.1). Non-polymer catechins were contained at 0.51 wt % in the purified tea extract, the recovery rate of non-polymer catechins from the tannase-treated solution (3) was 83.9%, and the percentage of gallate forms in the non-polymer catechins was 27.4 wt %. Further, the content of caffeine was 0.08 wt %, and the amount of gallic acid was 0.002 wt %. The non-polymer catechins in the solid content of the purified tea extract amounted to 62.5 wt %.

Comparative Example 4

Acid clay ("MIZUKA ACE #600", product of Mizusawa Chemical Industries, Ltd.; 100 g) was dispersed at stirring conditions of room temperature and 350 r/min in a 92.4 wt % aqueous solution of ethanol (800 g). After stirring was conducted for approximately 10 minutes, the "tannase-treated green tea extract 2" (200 g) obtained in (Comparative Example 3) was charged, and still at room temperature, stirring was continued for approximately 3 hours (pH 4.0). Subsequently, the formed precipitate and acid clay were filtered off by No. 2 filter paper. The resulting filtrate was brought into contact with activated carbon ("KURARAY COAL GLC", product of Kuraray Chemical Co., Ltd.; 30 g), and without a break, was filtered through a 0.2-μm membrane filter. Finally, deionized water (200 g) was added, ethanol was distilled off at 40° C. and 2.7 kPa, and then, the water content was adjusted to obtain a "purified green tea extract". In the resulting extract, non-polymer catechins were contained at 20.2 wt %. The recovery rate of non-polymer catechins from the "tannase-treated green tea extract 2" of Comparative Example 3 was 60.5%, and the percentage of gallate forms in the non-polymer catechins was 29.3 wt %. Further, the content of caffeine was 0.73 wt %, and the content of gallic acid was 2.56 wt %. The non-polymer catechins in the solid content of the purified tea extract amounted to 56.6 wt %.

The results of Examples 1-2 and Comparative Examples 1-4 are shown below in tables, in which Table 2 shows the analysis data of the tea extracts after the tannase treatment and Table 3 shows the analysis data of the purified tea extracts after the elution from the activated carbon.

TABLE 2

| Tannase treatment | | Example 1 Applied | Example 2 Applied | Comp. Ex. 1 Applied |
|---|---|---|---|---|
| <Analysis data of tea extracts after tannase treatment> | | | | |
| Content of non-polymer catechins | [wt %] | 0.94 | 0.94 | 0.89 |
| Content of caffeine | [wt %] | 0.19 | 0.19 | 0.20 |
| Content of gallic acid | [wt %] | 0.10 | 0.11 | 0.10 |
| Percentage of gallate forms in non-polymer catechins | [wt %] | 31.7 | 30.6 | 52.4 |
| Gallic acid/non-polymer catechins ratio | [—] | 0.11 | 0.12 | 0.11 |
| Reduction rate of gallate forms | [wt %] | 22.3 | 23.4 | 17.1 |

| Tannase treatment | | Comp. Ex. 2 Not applied | Comp. Ex. 3 Applied | Comp. Ex. 4 Applied |
|---|---|---|---|---|
| <Analysis data of tea extracts after tannase treatment> | | | | |
| Content of non-polymer catechins | [wt %] | 0.92 | 0.90 | 27.8 |
| Content of caffeine | [wt %] | 0.17 | 0.21 | 6.74 |
| Content of gallic acid | [wt %] | 0.01 | 0.11 | 3.58 |
| Percentage of gallate forms in non-polymer catechins | [wt %] | 51.1 | 30.3 | 30.3 |
| Gallic acid/non-polymer catechins ratio | [—] | 0.01 | 0.12 | 0.129 |
| Reduction rate of gallate forms | [wt %] | 0 | 22 | 22.0 |

TABLE 3

Analysis data of purified tea extracts after elution from activated carbon

| | | Example 1 | Example 2 | Comp. Ex. 1 |
|---|---|---|---|---|
| Kind of activate carbon | | SGP | GLC | Not used |
| pH of aqueous solution of alkali | [—] | 12.5 | 12.5 | — |
| Concentration of ethanol | [wt %] | — | — | — |
| Content of non-polymer catechins | [wt %] | 0.24 | 0.57 | — |
| Content of caffeine | [wt %] | 0 | 0 | — |
| Content of gallic acid | [wt %] | 0.010 | 0.020 | — |
| Caffeine/non-polymer catechins ratio | [—] | 0 | 0 | — |
| Gallic acid/non-polymer catechins ratio | [—] | 0.042 | 0.035 | — |
| Recovery rate of non-polymer catechins | [%] | 77 | 72 | — |
| pH adjustment method | | Ion exchange | Ion exchange | — |
| pH after adjustment (25° C.) | [—] | 3.1 | 2.8 | — |
| Percentage of gallate forms in non-polymer catechins | [wt %] | 32 | 30.4 | 52.4 |
| Non-polymer catechins in solid content | [wt %] | 58.0 | 56.0 | 32.3 |
| <Assessment of taste and flavor after sterilization> | Bitterness | Very slight | Very slight | Slight |
| | Sourness | None | None | Possessed |
| | Coarseness | No abnormal taste or smell | No abnormal taste or smell | Possessed |
| <Assessment of bitterness> | Quinine sulfate assessment | 5.5 | 5.3 | 8.0 |

| | | Comp. Ex. 2 | Comp. Ex. 3 | Comp. Ex. 4 |
|---|---|---|---|---|
| Kind of activate carbon | | GLC | SP70 | Not used |
| pH of aqueous solution of alkali | [—] | 14 | — | — |
| Concentration of ethanol | [wt %] | — | 20 | 92 |
| Content of non-polymer catechins | [wt %] | 0.49 | 0.51 | 20.2 |
| Content of caffeine | [wt %] | 0 | 0.08 | 0.73 |
| Content of gallic acid | [wt %] | 0.016 | 0.002 | 2.56 |
| Caffeine/non-polymer catechins ratio | [—] | 0 | 0.147 | 0.036 |
| Gallic acid/non-polymer catechins ratio | [—] | 0.032 | 0.004 | 0.127 |
| Recovery rate of non-polymer catechins | [%] | 65.0 | 83.9 | 60.5 |
| pH adjustment method | | Ion exchange | — | — |
| pH after adjustment (25° C.) | [—] | 2 | 2.1 | 3.3 |
| Percentage of gallate forms in non-polymer catechins | [wt %] | 48.6 | 27.4 | 29.3 |

TABLE 3-continued

| Analysis data of purified tea extracts after elution from activated carbon | | | | |
|---|---|---|---|---|
| Non-polymer catechins in solid content | [wt %] | 56.0 | 62.5 | 56.6 |
| <Assessment of taste and flavor after sterilization> | Bitterness | Slight | Very slight | Very slight |
| | Sourness | None | None | Possessed |
| | Coarseness | No abnormal taste or smell | No abnormal taste or smell | No abnormal taste or smell |
| <Assessment of bitterness> | Quinine sulfate assessment | 7.8 | 5.3 | 6.3 |

In Example 1 and Example 2, the recovery rates of non-polymer catechins were high both before and after the treatment, and purified tea extracts reduced in the percentage of non-polymer catechingallates, caffeine and gallic acid and improved in taste were successfully obtained. Comparative Example 1 was assessed to be inferior in bitterness, sourness and coarseness, Comparative Example 2 was assessed to be inferior in bitterness, Comparative Example 3 was great in the amount of caffeine, and Comparative Example 4 was great in the amounts of caffeine and gallic acid, and moreover, was assessed to be inferior in sourness.

Example 3

Hot water of 88° C. (45 kg) was added to the green tea leaves (produce of Kenya, large leaf variety; 3 kg). After batchwise extraction for 60 minutes under stirring, coarse filtration was conducted through a 100-mesh screen. To remove fine powder from the extract solution, a centrifugal separation operation was then performed to obtain a "green tea extract solution 4" (37.2 kg, pH 5.4) (the concentration of non-polymer catechins in the green tea extract solution=0.89 wt %, the percentage of gallate forms in the non-polymer catechins=52.3 wt %, the content of caffeine=0.17 wt %).

The green tea extract solution was held at a temperature of 15° C., and tannase ("TANNASE KTFH", product of Kikkoman Corporation; 500 U/g) was then added to the green tea extract solution to give a concentration of 430 ppm. The solution was held for 55 minutes. When the percentage of gallate forms had dropped to 32 wt %, the solution was heated to 90° C., at which the solution was held for 2 minutes to inactivate the enzyme so that the reaction was terminated (pH 5.2). Under conditions of 70° C. and 6.7 kPa, a concentration processing was performed to a Brix concentration of 20% by reduced-pressure concentration. Further, the concentrate was spray-dried to obtain a powdery "tannase-treated green tea extract 4" (0.9 kg). The resulting green tea extract had the following data—the content of non-polymer catechins: 29.0 wt %, the percentage of gallate forms in the non-polymer catechins: 31.7 wt %, the content of caffeine: 5.86 wt %, and the content of gallic acid: 3.09 wt %.

The "tannase-treated green tea extract 4" (10 g) was dissolved under stirring at 25° C. for 30 minutes in deionized water (300 g) (tannase-treated solution (4)). The resulting tannase-treated solution had the following data—the content of non-polymer catechins: 0.94 wt %, the percentage of gallate forms in the non-polymer catechins: 31.1 wt %, the content of caffeine: 0.19 wt %, and the content of gallic acid: 0.1 wt %.

Activated carbon, "TAIKO SGP" (product of Futamura Chemical Co., Ltd.; 40 mL) was packed in a stainless steel column 1 (22 mm inner diameter×105 mm height, volume: 40 mL). The tannase-treated solution (4) (200 g, 5 times volume relative to the activated carbon) was passed at $SV=2$ ($h^{-1}$) through the column 1, and the outflow was discarded. The column 1 was then washed at $SV=(h^{-1})$ with water (80 mL, 2 times volume relative to the activated carbon). After washing it with water, a 25 wt % aqueous solution of ethanol (320 mL, 8 times volume relative to the activated carbon) was passed at $SV=2$ ($h^{-1}$) to obtain a purified tea extract (320 g). Non-polymer catechins were contained at 0.32 wt % in the purified tea extract, the recovery rate of non-polymer catechins from the tannase-treated solution (4) was 54%, and the percentage of gallate forms in the non-polymer catechins was 9.5 wt %. Further, the content of caffeine was 0 wt %, and the content of gallic acid was 0.032 wt %. Non-polymer catechins in the solid content of the purified tea extract amounted to 59 wt %.

Further, ethanol was distilled off at 40° C. and 2.7 kPa by a reduced-pressure concentration, and subsequently, the water content was adjusted to obtain a "purified product 3". The color tone of the resulting purified product was 0.016.

Example 4

The "green tea extract solution 4" obtained in Example 3 was held at a temperature of 15° C., and tannase ("TANNASE KTFH", product of Kikkoman Corporation; 500 U/g) was then added to the green tea extract solution to give a concentration of 430 ppm. The solution was held for 70 minutes. When the percentage of gallate forms had dropped to 15.5 wt %, the solution was heated to 90° C., at which the solution was held for 2 minutes to inactivate the enzyme so that the reaction was terminated (pH 4.9). Under conditions of 70° C. and 6.7 kPa, a concentration processing was performed to a Brix concentration of 20% by reduced-pressure concentration. Further, the concentrate was spray-dried to obtain a powdery "tannase-treated green tea extract 5" (0.9 kg).

The "tannase-treated green tea extract 5" (12 g) was dissolved under stirring at 25° C. for 30 minutes in deionized water (300 g) (tannase-treated solution (5)). The resulting tannase-treated solution had the following data—the content of non-polymer catechins: 0.98 wt %, the percentage of gallate forms in the non-polymer catechins: 15.0 wt %, the content of caffeine: 0.19 wt %, and the content of gallic acid: 0.19 wt %.

Activated carbon, "TAIKO SGP" (product of Futamura Chemical Co., Ltd.; 40 mL) was packed in a stainless steel column 2 (22 mm inner diameter×105 mm height, volume: 40 mL). The tannase-treated solution (5) (200 g, 5 times volume relative to the activated carbon) was passed at $SV=2$ ($h^{-1}$) through the column 2, and the outflow was discarded. The column 2 was then washed at $SV=2$ ($h^{-1}$) with water (240 mL, 6 times volume relative to the activated carbon). After washing it with water, a 30 wt % aqueous solution of ethanol (320 mL, 8 times volume relative to the activated carbon) was passed at $SV=2$ ($h^{-1}$) to obtain a purified tea extract (320 g). Non-polymer catechins were contained at 0.38 wt % in the purified tea extract, the recovery rate of non-polymer catechins from the tannase-treated solution (5) was 62%, and the percentage of gallate forms in the non-polymer catechins was 2.8 wt %. Further, the content of caffeine was 0 wt %, and the content of gallic acid was 0.015 wt %. Non-polymer catechins in the solid content of the purified tea extract amounted to 73 wt %.

Further, ethanol was distilled off at 40° C. and 2.7 kPa by a reduced-pressure concentration, and subsequently, the water content was adjusted to obtain a "purified product 4". The color tone of the resulting purified product was 0.003.

Example 5

Using a 40 wt % aqueous solution of ethanol as an eluent, a similar operation as in Example 4 was performed to obtain a purified tea extract (320 g). Non-polymer catechins were contained at 0.45 wt % in the purified tea extract, the recovery rate of non-polymer catechins from the tannase-treated solution (5) was 73.1%, and the percentage of gallate forms in the non-polymer catechins was 7.8 wt %. Further, the content of caffeine was 0.01 wt %, and the content of gallic acid was 0.009 wt %. Non-polymer catechins in the solid content of the purified tea extract amounted to 69 wt %.

Further, ethanol was distilled off at 40° C. and 2.7 kPa by a reduced-pressure concentration, and subsequently, the water content was adjusted to obtain a "purified product 5". The color tone of the resulting purified product was 0.019.

Example 6

The "tannase-treated green tea extract 4" (11 g) was dissolved under stirring at 25° C. for 30 minutes in deionized water (300 g) (tannase-treated solution (6)). The resulting tannase-treated solution had the following data—the content of non-polymer catechins: 1.05 wt %, the percentage of gallate forms in the non-polymer catechins: 31.6 wt %, the content of caffeine: 0.21 wt %, and the content of gallic acid: 0.11 wt %.

Using the starting material, similar work as in Example 5 was performed to obtain a purified tea extract (320 g). Non-polymer catechins were contained at 0.46 wt % in the purified tea extract, the recovery rate of non-polymer catechins from the tannase-treated solution (6) was 70.3%, and the percentage of gallate forms in the non-polymer catechins was 27 wt %. Further, the content of caffeine was 0.022 wt %, and the content of gallic acid was 0.009 wt %. Non-polymer catechins in the solid content of the purified tea extract amounted to 66 wt %.

Further, ethanol was distilled off at 40° C. and 2.7 kPa by a reduced-pressure concentration, and subsequently, the water content was adjusted to obtain a "purified product 6". The color tone of the resulting purified product was 0.027.

Comparative Example 5

Hot water of 90° C. (27 kg) was added to the green tea leaves (Yunnan Province, China; large leaf variety; 1.8 kg). After batchwise extraction for 30 minutes under stirring, a coarse filtration was conducted through a 100-mesh screen. Subsequent to a centrifugal separation operation, the filtration was conducted through No. 2 filter paper to obtain a "green tea extract solution 7" (20.4 kg, pH 5.3) (the concentration of non-polymer catechins in the green tea extract solution=0.96 wt %, the percentage of gallate forms in the non-polymer catechins=69.5 wt %, the content of caffeine=0.24 wt %, the content of gallic acid=0.01 wt %).

The green tea extract solution was set to a temperature of 25° C., and tannase ("TANNASE KTFH", product of Kikkoman Corporation; 500 U/g) was then added to the green tea extract solution to give a concentration of 300 ppm. The solution was held for 85 minutes. When the percentage of gallate forms had dropped to 52.4 wt %, the solution was heated to 90° C., at which the solution was held for 2 minutes to inactivate the enzyme so that the reaction was terminated (pH 4.8). The resulting "tannase-treated solution (7) had the following data—the content of non-polymer catechins: 0.89 wt %, the percentage of gallate forms in the non-polymer catechins: 52.4 wt %, the content of caffeine: 0.20 wt %, and gallic acid: 0.10 wt %. The color tone of the treated solution was 0.7.

Comparative Example 6

The "green tea extract solution 4" obtained in Example 4 was held at a temperature of 15° C., and tannase ("TANNASE KTFH", product of Kikkoman Corporation; 500 U/g) was added to the green tea extract solution to give a concentration of 430 ppm. The solution was held for 55 minutes. When the percentage of gallate forms had dropped to 30.5 wt %, the solution was heated to 90° C., at which the solution was held for 2 minutes to inactivate the enzyme so that the reaction was terminated (pH 5.1). A concentration processing was then performed under conditions of 70° C. and 6.7 kPa to a Brix concentration of 20% by a reduced-pressure concentration. Further, the concentrate was spray-dried to obtain a powdery "tannase-treated green tea extract 8" (0.91 kg). The resulting green tea extract had the following data—the content of non-polymer catechins: 27.8 wt %, the percentage of gallate forms in non-polymer catechins: 30.3 wt %, the content of caffeine: 6.74 wt %, and gallic acid: 3.58 wt %.

The "tannase-treated green tea extract 8" (285 g) was dissolved under stirring at 25° C. for 30 minutes in deionized water (8,550 g) (tannase-treated solution (8)). The resulting tannase-treated solution had the following data—the content of non-polymer catechins: 0.90 wt %, the percentage of gallate forms in non-polymer catechins: 30.3 wt %, the content of caffeine: 0.21 wt %, and the content of gallic acid: 0.11 wt %.

A synthetic adsorbent "SP-70" (product of Mitsubishi Chemical Corporation; 2,048 mL) was packed in a stainless steel column 3 (110 mm inner diameter×230 mm height, volume: 2,185 mL). The tannase-treated solution (8) (8,191 g, 4 times volume relative to the synthetic adsorbent) was passed at SV=1 ($h^{-1}$) through the column, and the outflow was discarded. The column 3 was then washed at SV=2 ($h^{-1}$) with water (2,048 mL, same volume relative to the synthetic adsorbent). After washing it with water, a 20 wt % aqueous solution of ethanol (12,287 mL, 6 times volume relative to the synthetic adsorbent) was passed at SV=2 ($h^{-1}$) through the column 3 to obtain a purified tea extract (12,090 g, pH 2.1). Non-polymer catechins were contained at 0.51 wt % in the purified tea extract, and the percentage of gallate forms in the non-polymer catechins was 27.4 wt %. Further, the content of caffeine was 0.08 wt %, and the content of gallic acid was 0.002 wt %. The non-polymer catechins in the solid content of the purified tea extract amounted to 62.5 wt %.

Further, ethanol was distilled off at 40° C. and 2.7 kPa by a reduced-pressure concentration, and subsequently, the water content was adjusted to obtain a "purified product 8". The color tone of the resulting purified product was 0.38.

Comparative Example 7

Acid clay ("MIZUKA ACE #600", product of Mizusawa Chemical Industries, Ltd.; 100 g) was dispersed at stirring conditions of room temperature and 350 r/min in a 92.4 wt % aqueous solution of ethanol (800 g). After stirring was conducted for approximately 10 minutes, the "tannase-treated green tea extract 8" (200 g) obtained in Comparative Example 6 was charged, and still at room temperature, stirring was continued for approximately 3 hours (pH 4.0). Subsequently, the formed precipitate and acid clay were filtered off by No. 2 filter paper. The resulting filtrate was brought into contact with activated carbon ("KURARAY COAL GLC", product of Kuraray Chemical Co., Ltd.; 30 g), and without a break, was filtered through a 0.2-µm membrane filter. Finally, deionized water (200 g) was added, ethanol was distilled off at 40° C. and 2.7 kPa, and then, the water content was adjusted to obtain a "purified product 9". In the resulting purified tea extract, the non-polymer catechins were contained at 20.2 wt %. The recovery rate of non-polymer catechins from the "tannase-treated green tea extract 8" was 60.5%, and the percentage of gallate forms in the non-polymer catechins was 29.3 wt %. Further, the content of caffeine was 0.73 wt %, and the content of gallic acid was 2.56 wt %. The non-polymer catechins in the solid content of the purified tea extract amounted to 56.6 wt %. The color tone of the resulting purified product was 0.03.

The results of Examples 3-6 and Comparative Examples 5-7 are shown below in tables, in which Table 4 shows the analysis data of the tea extracts after the tannase treatment and Table 5 shows the analysis data of the purified tea extracts after the elution from the activated carbon.

TABLE 4

| Tannase treatment | | Example 3 Applied | Example 4 Applied | Example 5 Applied | Example 6 Applied |
|---|---|---|---|---|---|
| <Analysis data of tea extracts after tannase treatment> | | | | | |
| Content of non-polymer catechins | [wt %] | 0.94 | 0.98 | 0.98 | 1.05 |
| Content of caffeine | [wt %] | 0.19 | 0.19 | 0.19 | 0.21 |
| Content of gallic acid | [wt %] | 0.10 | 0.19 | 0.19 | 0.11 |
| Percentage of gallate forms in non-polymer catechins | [wt %] | 31.1 | 15 | 15.0 | 31.6 |
| Gallic acid/non-polymer catechins ratio | [—] | 0.11 | 0.20 | 0.20 | 0.10 |
| Reduction rate of gallate forms | [wt %] | 22.9 | 39.0 | 39.0 | 22.4 |

| Tannase treatment | | Comp. Ex. 5 Applied | Comp. Ex. 6 Applied | Comp. Ex. 7 Applied |
|---|---|---|---|---|
| <Analysis data of tea extracts after tannase treatment> | | | | |
| Content of non-polymer catechins | [wt %] | 0.89 | 0.90 | 27.8 |
| Content of caffeine | [wt %] | 0.20 | 0.21 | 6.74 |
| Content of gallic acid | [wt %] | 0.10 | 0.11 | 3.58 |
| Percentage of gallate forms in non-polymer catechins | [wt %] | 52.4 | 30.3 | 30.3 |
| Gallic acid/non-polymer catechins ratio | [—] | 0.11 | 0.12 | 0.129 |
| Reduction rate of gallate forms | [wt %] | 17.1 | 22 | 22.0 |

TABLE 5

| Analysis data of purified tea extracts after elution from activated carbon | | | | | |
|---|---|---|---|---|---|
| | | Example 3 | Example 4 | Example 5 | Example 6 |
| Kind of activate carbon | | SGP | SGP | SGP | SGP |
| Concentration of ethanol | [wt %] | 25 | 30 | 40 | 40 |
| Content of non-polymer catechins | [wt %] | 0.32 | 0.38 | 0.45 | 0.46 |
| Content of caffeine | [wt %] | 0 | 0 | 0.01 | 0.022 |
| Content of gallic acid | [wt %] | 0.032 | 0.015 | 0.009 | 0.009 |
| Caffeine/non-polymer catechins ratio | [—] | 0 | 0 | 0.018 | 0.048 |
| Gallic acid/non-polymer catechins ratio | [—] | 0.100 | 0.040 | 0.020 | 0.020 |
| Recovery rate of non-polymer catechins | [%] | 54 | 62 | 73.1 | 70.3 |
| pH after adjustment (25° C.) | [—] | — | — | 3.8 | 3.5 |
| Percentage of gallate forms in non-polymer catechins | [wt %] | 9.5 | 2.8 | 7.8 | 27 |
| Non-polymer catechins in solid content | [wt %] | 59.0 | 73.0 | 69.0 | 66.0 |
| Color tone [175 mg/100 mL] | [450 nmabs] | 0.016 | 0.003 | 0.019 | 0.027 |
| <Assessment of taste and flavor after sterilization> | Bitterness | None | None | None | Very slight |
| | Sourness | None | None | None | None |
| | Coarseness | No abnormal taste or smell | No abnormal taste or smell | No abnormal taste or smell | No abnormal taste or smell |
| <Assessment of bitterness> | Quinine sulfate assessment | 5.0 | 5.0 | 5.0 | 5.5 |

| | | Comp. Ex. 5 | Comp. Ex. 6 | Comp. Ex. 7 |
|---|---|---|---|---|
| Kind of activate carbon | | Not used | SP70 | Not used |
| Concentration of ethanol | [wt %] | — | 20 | 92 |
| Content of non-polymer catechins | [wt %] | — | 0.51 | 20.2 |

TABLE 5-continued

Analysis data of purified tea extracts after elution from activated carbon

| | | | | |
|---|---|---|---|---|
| Content of caffeine | [wt %] | — | 0.08 | 0.73 |
| Content of gallic acid | [wt %] | — | 0.002 | 2.56 |
| Caffeine/non-polymer catechins ratio | [—] | — | 0.147 | 0.036 |
| Gallic acid/non-polymer catechins ratio | [—] | — | 0.004 | 0.127 |
| Recovery rate of non-polymer catechins | [%] | — | 83.9 | 60.5 |
| pH after adjustment (25° C.) | [—] | — | 2.1 | 3.3 |
| Percentage of gallate forms in non-polymer catechins | [wt %] | 52.4 | 27.4 | 29.3 |
| Non-polymer catechins in solid content | [wt %] | 32.3 | 62.5 | 56.6 |
| Color tone [175 mg/100 mL] | [450 nmabs] | 0.7 | 0.38 | 0.003 |
| <Assessment of taste and flavor after sterilization> | Bitterness Sourness Coarseness | Slight Possessed Possessed | Very slight None No abnormal taste or smell | Very slight Possessed No abnormal taste or smell |
| <Assessment of bitterness> | Quinine sulfate assessment | 8.0 | 5.3 | 6.3 |

In Examples 3-6, the purified tea extracts reduced in the percentage of gallate forms in non-polymer catechins, caffeine and gallic acid, improved in taste and having good color tones were successfully obtained. Comparative Example 5 was assessed to be inferior in bitterness, sourness, coarseness and color tone, Comparative Example 6 was assessed to be inferior in the amount of caffeine and color tone, and Comparative Example 7 was assessed to be inferior in gallic acid and sourness.

Example 7

Using the purified green tea extract of Example 1 or 3, the beverage described in Table 6 was prepared for packaging application. Under the Food Sanitation Act of Japan, the beverage was subjected to sterilization treatment and then to hot-pack filling so that a packaged beverage was produced.

After the produced packaged beverage was stored at 37° C. for 30 days, it was assessed. It was good in external appearance and the stability of taste.

TABLE 6

| Names of materials | Added amounts (wt %) |
|---|---|
| Sugar | 1.50 |
| Salt | 0.33 |
| Sweetener | 0.01 |
| VC | 0.05 |
| Fruit extract | 0.10 |
| Flavoring | 0.20 |
| Purified green tea extract (Example 1 or 3) | 70.83 |
| Deionized water | Balance |
| Total | 100.00 |

The invention claimed is:

1. A process for producing a purified tea extract, the process comprising hydrolyzing a tea extract, allowing the hydrolyzed tea extract to adsorb on an activated carbon, and then contacting a basic aqueous solution or an aqueous solution of an organic solvent with the activated carbon, thereby eluting non-polymer catechins and producing the purified tea extract, wherein when the basic aqueous solution is contacted with the activated carbon to elute the non-polymer catechins, a flow rate of space velocity (SV) is from 2 to 10 [$h^{-1}$] and a flow rate is from 1 to 30 [v/v], wherein when the aqueous solution of an organic solvent is contacted with the activated carbon to elute the non-polymer catechins, a flow rate of space velocity (SV) is from 0.1 to 10 [$h^{-1}$] and a flow rate is from 1 to 15 [v/v], and wherein the activated carbon has an average pore size of from 0.5 to 10 nm, a pore volume of from 0.01 to 2.5 mL/g, and a specific surface area of from 800 to 2,000 $m^2/g$.

2. The process according to claim 1, wherein the hydrolysis is conducted with an enzyme, a fungus or a culture having a tannase activity.

3. The process according to claim 1 or 2, wherein after said contacting the basic aqueous solution with the activated carbon to elute the non-polymer catechins, an eluate is adjusted to a pH 7 or lower.

4. The process according to claim 1, wherein after said hydrolyzing the tea extract, the hydrolyzed tea extract is allowed to adsorb on the activated carbon, the activated carbon is washed, and then, the basic aqueous solution or the aqueous solution of the organic solvent is contacted with the activated carbon, thereby eluting the non-polymer catechins.

5. The process according to claim 1, wherein a decrease in a percentage of gallate forms in the non-polymer catechins by the hydrolysis of the tea extract is 5 wt % or more based on the tea extract before the hydrolysis.

6. The process according to claim 1, wherein (i) a content of the non-polymer catechins in a solid content is from 25 to 95 wt %, (ii) a content of gallates in the non-polymer catechins is from 0 to 70 wt %, (iii) a ratio of gallic acid to the non-polymer catechins is from 0 to 0.1, and (iv) a ratio of caffeine to the non-polymer catechins is from 0 to 0.14, in the produced purified tea extract.

7. The process according to claim 2, wherein the enzyme or culture having a tannase activity is used for said hydrolyzing and a content of the enzyme or culture having a tannase activity is from 0.01 to 10 wt. % based on the non-polymer catechins in the tea extract.

8. The process according to claim 2, wherein the enzyme or culture having a tannase activity is used for said hydrolyzing and an amount of the added enzyme or culture having a tannase activity is from 1 to 300 Units/g of non-polymer catechins based on the non-polymer catechins in the tea extract.

9. The process according to claim 2, wherein the enzyme or culture having a tannase activity is used for hydrolysis and a treatment temperature with the enzyme or culture having a tannase activity is from 0 to 70° C.

10. The process according to claim 2, wherein the enzyme or culture having a tannase activity is used for said hydrolyzing, the method further comprises inactivating the enzyme of culture having a tannase activity at a temperature of from 70 to 100° C.

11. The process according to claim 2, wherein the fungus is used for said hydrolyzing and a content of the fungus is from 0.1 to 22 wt. % in the tea extract containing the non-polymer catechins.

12. The process according to claim 2, wherein the fungus is used for said hydrolyzing and a treatment temperature with the fungus is from 45 to 70° C.

13. The process according to claim 1, wherein the tea extract passes through the activated carbon at a flow rate of space velocity (SV) of from 0.5 to 10 $[h^{-1}]$ and at a flow rate of from 0.5 to 20 [v/v].

14. The process according to claim 1, further compositing decolorizing the eluted non-polymer catechins.

* * * * *